United States Patent [19]

Warren

[11] Plant 4,698

[45] Apr. 21, 1981

[54] BLUEGRASS PLANT

[75] Inventor: Benedict O. Warren, Palos Hills, Ill.

[73] Assignee: Warren's Turf Nursery, Inc., Palos Hills, Ill.

[21] Appl. No.: 70,273

[22] Filed: Aug. 27, 1979

[51] Int. Cl.[3] ..... A01H 5/00
[52] U.S. Cl. ..... Plt./88
[58] Field of Search ..... Plt./88

*Primary Examiner*—Robert E. Bagwill
*Assistant Examiner*—James R. Feyrer
*Attorney, Agent, or Firm*—Townsend and Townsend

[57] ABSTRACT

A new and distinct variety of Kentucky Bluegrass (*Poa pratensis* L.) characterized particularly by very good turf performance, excellent shade tolerance, excellent uniformity, and high resistance to most of the common bluegrass diseases. The plant tolerates a close cut, maintains a medium dark green color and does very well in early spring.

3 Drawing Figures

1

The present invention relates to a new and distinct variety of Kentucky bluegrass plant which exhibits excellent shade tolerance, a relative degree of tolerance to Fusarium blight and smut, high tiller density and excellent turf quality as indicated by data taken at research centers throughout the country.

The new variety was selected from space planted open pollinated A20 Kentucky bluegrass plants that were being grown at Palos Hills, Ill., in 1967. The variety in question exhibited excellent aggressiveness and uniformity as well as a medium fine leaf texture that set it apart from the other grasses. The grass was asexually propagated by rhizomes and tillers at Palos Hills, and was labeled A20-6 or WTN-H6 with the WTN-H6 being the official designated experimental name. Since that time, the grass has been tested using both vegetative material of the variety as well as seeded material of the said plant without any differences being noted between the two methods of propagating or increasing the stock of the new plant. The variety is being maintained vegetatively at Suisun City, Calif.

WTN-H6 Kentucky Bluegrass (*Poa pratensis*) is perennial with a high degree of uniformity in its growth habit that makes it very attractive at cutting heights of 1.3 cm., to the standard height of 2.5 to 3.7 cm. It is a turf type that has a leafy, medium dark green color with a tiller density of 1500 plus tillers per square foot. Of special importance is its ability to withstand shade of plus 65 percent. The new variety exhibits good to excellent resistance to the fungi *Fusarium roseum, Fusarium tricintum, Ustilago striiformis, Drechslera poae* and *Erysiphe graminia.*

The WTN-H6 is new and distinct from other grasses based on the aforementioned characteristics. Further value and importance of this invention will be seen as more detail is given of the above-mentioned qualities together with other information that will be detailed such as the following illustrations and detailed descriptions.

Figure 1:
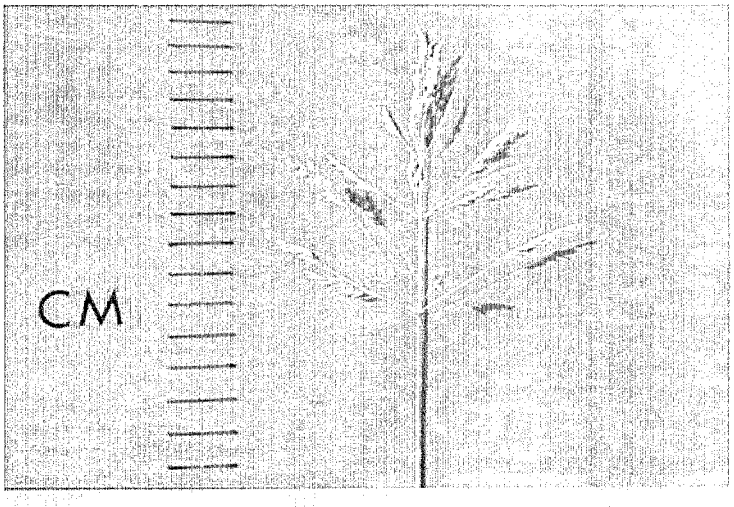
FIG. 1 shows a panicle of the new variety three weeks after the completion of flowering.
Figure 2:
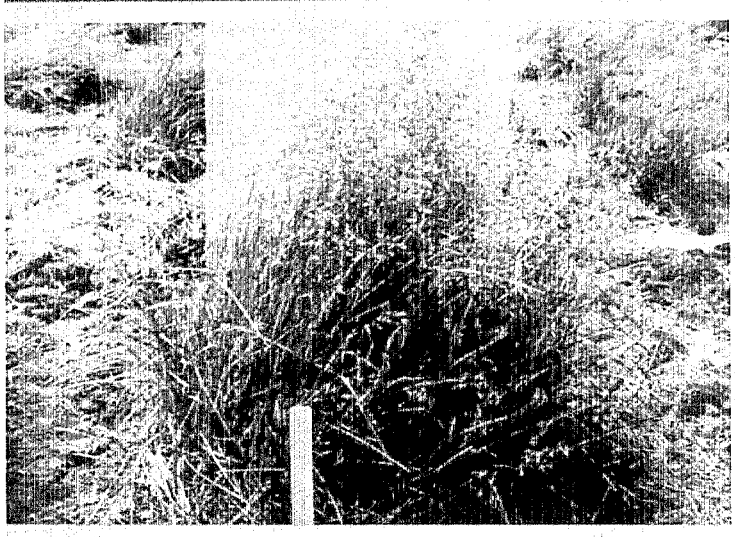
FIG. 2 shows a plant after the completion of flowering.
Figure 3:
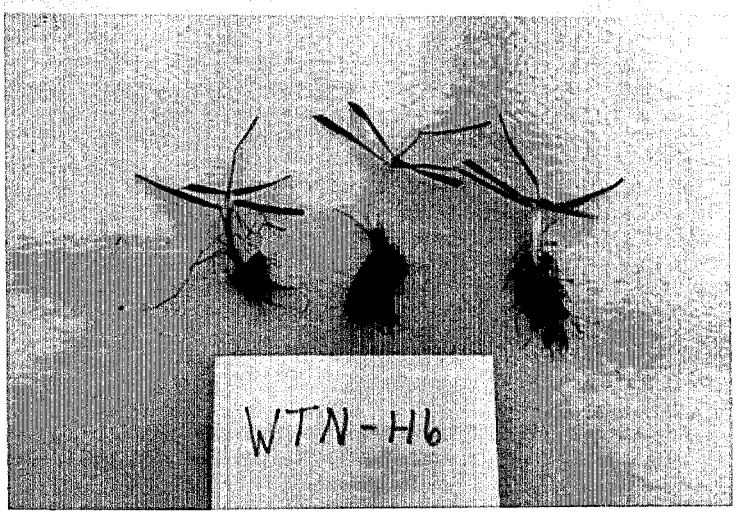
FIG. 3 shows some typical tillers of WTN-H6 extracted from a closely mowed turf.

The WTN-H6 exhibits its uniqueness in the following ways:

2

(1) excellent shade tolerance;
(2) a leafy turf type capable of withstanding a close cut;
(3) petite panicles and spikelets;
(4) excellent rhizome and tiller development;
(5) excellent turf quality;
(6) an attractive medium dark green color;
(7) excellent density;
(8) moderately fine leaf texture.

The color references herein are to *Royal Horticultural Society Color Chart* (1941), by Robert F. Wilson. The readings were taken on July 24, 1979 on mature tillers using the first leaf on each tiller on heavily watered, fertilized turf, at Suisun City, Calif.

Plant Description: Under conditions such as those experienced in the summer of 1976 at Palos Hills, Ill., and in the summer of 1978 at Hubbard, Oreg., the following plant description of WTN-H6 can be made based on average measurements.

Under conditions of flowering, the culms of the new invention are moderately bending and are usually three noded. The stems are cylindrical, smooth, relatively slim, and moderately shiny to glossy with a medium green color. The culms are tufted, average 61.1 cm. in height when uncut, have a panicle length of 13.8 cm. a flag leaf length of 12.1 cm. and a flag leaf width of 4.9 mm. The leaves are medium to dark green in color (137 A Green Group) and the sheaths are smooth and hairless with an average ligule length of 0.5 mm. The panicles are semi-pyramidal with the main axis erect and the branches semi-erect even during seed set. The spikelets are delicate in nature; average 3.8 mm. in length with about 4.5 branches at the lower branches of the panicle. There are approximately 3.9 florets per spikelet. The spikelets are ovate and compressed with the upper spikelets in clusters and close branching and the lower branching wider spaced. The glumes are unequal with the upper ovate to eliptic averaging 2.0 mm. and the lower averaging 2.1 mm. Lemmas are overlapping, oblong to ovate measuring approximately 2.6 mm. in length and there are fine hairs at the base and the lower half of the lemmas. The paleas average out to 2.3 mm. in length. The caryopses are tightly enclosed in the lemma and palea.

Under mowing (3.2 cm.), the number of tillers per square inch averages 23.3 with 3.8 leaves per tiller and each leaf (2d leaf) measuring 2.1 mm. on the average.

The ligules are short (not extending beyond the edge of the collar) and the leaf is medium to dark green in color (137 A Green Group) with a keel shape and boat-shaped tip. The chromosome count is approximately 2n=36.

Turf Characteristics: The new variety has consistently maintained a high quality turf relative to other Kentucky bluegrasses in test plots located across the country. It is a fine textured bluegrass that is vigorous and aggressive. Overall turf performance with WTN-H6 as compared with other recognized bluegrasses are listed in Tables One, Two, Three, Four and Five.

TABLE ONE

Comparisons for Relative Turf Quality of WTN-H6 and Other Bluegrasses at Palos Hills, Illinois:

| Variety | 1976*1 | 1977*2 | 1978*3 |
|---|---|---|---|
| WTN-H6 | 5.5 | 5.0 | 5.9 |
| A20 | 5.3 | 3.7 | 5.0 |
| Adelphi | 4.8 | 4.0 | 4.7 |
| Baron | 4.3 | 4.3 | 4.7 |
| Glade | 4.7 | 4.0 | 4.1 |

*Scale: 9 equals best
[1]Based on 6 observations.
[2]Based on 9 observations.
[3]Based on 15 observations

TABLE TWO

Relative Comparisons of WTN-H6 and Other Bluegrasses for Turf Quality, Density, Color, and Drought Tolerance Taken in 1978 on Replicated Plots Established in 1975 at Anderson, Indiana:

| Variety | Turf[1] Quality | Density[2] | Color[3] | Drought[4] Tolerance |
|---|---|---|---|---|
| WTN-H6 | 5.6 | 3.7 | 4.0 | 3.7 |
| Glade | 4.0 | 3.0 | 2.0 | 2.5 |
| Adelphi | 4.3 | 3.5 | 3.3 | 3.7 |
| Brunswick | 4.6 | 3.0 | 2.3 | 2.7 |
| Baron | 4.0 | 2.7 | 2.7 | 2.7 |
| Touchdown | 3.9 | 2.7 | 2.0 | 1.7 |

[1]Scale: 9 equals best. Based on 6 observations.
[2]Scale: 5 equals best. Based on 3 observations.
[3]Scale: 5 equals best. Based on 3 observations. Drought tolerance was a factor.
[4]Scale: 5 equals best. Based on 3 observations.
Three weeks of temperatures in the 90's preceeded these readings.

TABLE THREE

Relative Comparisons for Turf Performance, Stem Rust, and Dollar Spot Tolerances for WTN-H6 and Other Bluegrasses Taken in 1976 at Adelphia, New Jersey on Plots Established in 1974 by Rutgers University.[1]

| Variety | Rust[2] | Dollar Spot[3] Mean | Turf[4] Performance |
|---|---|---|---|
| WTN-H6 | 1.0 | 17 | 6.2 |
| A34 | 1.5 | 56 | 6.0 |
| Nugget | 2.5 | 231 | 5.6 |
| Victa | 1.9 | 48 | 6.4 |
| Merion | 7.5 | 43 | 5.5 |
| Baron | 2.5 | 75 | 5.9 |
| Touchdown | 6.3 | 101 | 6.3 |

[1]Turf plots for WTN-H6 were in the same area as the commercial grasses.
[2]Scale: 1 equals best; 9 equals worst.
[3]Average number of spots.
[4]Scale: 9 equals best; 1 equals worst.

TABLE FOUR

Heat Tolerance, General Appearance, and Density Ratings for WTN-H6 and Other Blugrasses Observed in 1978 at New Mexico State at Las Cruces, New Mexico.

| Variety | Heat Tolerance[1] | General Appearance[2] | Density[3] |
|---|---|---|---|
| WTN-H6 | 7.0 | 6.2 | 7.0 |
| Glade | 7.0 | 7.0 | 7.7 |
| Touchdown | 6.5 | 5.8 | 5.7 |
| A34 | 6.0 | 6.8 | 7.3 |

TABLE FOUR-continued

Heat Tolerance, General Appearance, and Density Ratings for WTN-H6 and Other Blugrasses Observed in 1978 at New Mexico State at Las Cruces, New Mexico.

| Variety | Heat Tolerance[1] | General Appearance[2] | Density[3] |
|---|---|---|---|
| Baron | 6.0 | 6.0 | 6.7 |

[1]Scale: 1 equals least to 9 equals most; based on averages for general appearance and color scores taken on July 5 following 17 days of 100 degree temperatures or above during late June and early July.
[2]Scale: 1 equals poor to 9 equals best; based on 5 observation.
[3]Scale: 1 equals least to 9 equals most dense; based on 3 observations.

TABLE FIVE

General Quality Ratings of WTN-H6 and Other Bluegrasses on Replicated Plots Estabished in 1972 at the University of Illinois.

| Cultivar | 3/16/77* | 4/28/77* | 6/24/77* |
|---|---|---|---|
| WTN-H6 | 4.3 | 2.3 | 2.0 |
| Adelphi | 4.0 | 4.0 | 2.3 |
| Baron | 4.0 | 4.0 | 2.3 |
| Brunswick | 4.3 | 3.3 | 2.3 |
| Fylking | 4.3 | 4.0 | 3.0 |
| Nugget | 6.3 | 4.3 | 2.0 |
| Glade | 4.7 | 4.7 | 2.3 |
| **Cultivar** | **7/14/77*** | **8/2/77*** | **10/11/77*** |
| WTN-H6 | 2.0 | 2.0 | 1.7 |
| Adelphi | 2.3 | 4.0 | 3.0 |
| Baron | 3.7 | 3.0 | 4.0 |
| Brunswick | 2.3 | 3.7 | 5.3 |
| Fylking | 4.3 | 5.3 | 5.7 |
| Nugget | 3.7 | 5.3 | 6.0 |
| Glade | 2.7 | 2.7 | 4.7 |

*Quality was based on a scale of 1-9 with 1 being best.

WTN-H6 has thus far been able to withstand adverse weather conditions very favorably. It has good heat and drought tolerance as indicated by Tables Two and Four. It maintains a good color under dry conditions. In hot dry conditions such as experienced in Suisun City, Calif., it has survived very well for over six years.

In shade trials, WTN-H6 is one of a few select bluegrasses that maintain quality. Tables Six and Seven indicate the relative turf qualities of the new invention to other bluegrasses.

TABLE SIX

Relative Comparisons of Shade Tolerance for WTN-H6 and Other Bluegrasses Taken in 1976, 1977, and overall Average for 1976, 1977 and 1978 at Columbus, Ohio, on Plots Established in 1975.

| Variety | Turf*(76) Quality | Turf*(77) Quality | Overall *(76, 77, & 78) |
|---|---|---|---|
| WTN-H6 | 5.1 | 5.0 | 5.3 |
| Nugget | 5.0 | 4.3 | 5.2 |
| Glade | 4.9 | 5.0 | 4.4 |
| A34 | 4.4 | 4.3 | 4.4 |
| Victa | 3.1 | 2.0 | 2.8 |
| Merion | 3.0 | 3.3 | 2.9 |
| Bristol | 5.5 | 4.5 | 5.1 |

*Scale: 1 equals worst; 9 equals best.

TABLE SEVEN

Relative Comparisons of Shade Tolerances for WTN-H6 and Other Bluegrasses Taken in 1974, 1975 and 1976 at Palos Hills, Illinois, Under Conditions of Artificial Shade of 65 percent.

| Variety | Turf Quality 1974 (8)[1] | Turf Quality 1975 (12[1 2] | Turf Quality 1976 (4)[1] |
|---|---|---|---|
| WTN-H6 | 7.8 | 5.7 | 5.8 |
| Nugget | 6.7 | 3.2 | 3.0 |
| Glade | 6.5 | 3.2 | 3.8 |

TABLE SEVEN-continued

Relative Comparisons of Shade Tolerances for WTN-H6 and Other Bluegrasses Taken in 1974, 1975 and 1976 at Palos Hills, Illinois, Under Conditions of Artificial Shade of 65 percent.

| Variety | Turf Quality 1974 (8)[1] | Turf Quality 1975 (12[1 2] | Turf Quality 1976 (4)[1] |
|---|---|---|---|
| A34 | 7.0 | 4.8 | 5.3 |

( ) Number of observations.

[1]Scale: 1 equals poorest; 9 equals best.

[2]No water applied to plots, very dry year.

Disease Tolerances: A comparison WTN-H6 with other bluegrasses for resistance or tolerance to various turfgrass diseases are indicated in Tables Three, Eight, Nine and Ten.

TABLE EIGHT

Relative Comparisons for Fusarium Blight Resistance and Relative Agressiveness or Percent Cover of the Grasses in 1975 and 1978 at the Danville Country Club, Danville, Illinois.

| Variety | Fusarium*(75) | % Cover (75) | % Cover (78) |
|---|---|---|---|
| WTN-H6 | 1.5 | 83 | 117 |
| A20 | 2.2 | 87 | 106 |
| Baron | 2.5 | 41 | 82 |
| Fylking | 6.8 | 70 | 82 |

*Scale: 1 equals best; 9 equals worst.

Based on 3 replications.

Percent cover is based on a base of 100 percent which is the original size of the plots.

TABLE NINE

Relative Comparisons for Resistance to Powdery Mildew for WTN-H6 and Other Bluegrasses on Plots Established at Ohio State University in 1975.

| Variety | Disease Rating* (76) | Disease Rating* (77) |
|---|---|---|
| WTN-H6 | 2.3* | 1.0* |
| Nugget | 2.0* | 2.0* |
| Glade | 1.7* | 1.3* |
| A34 | 5.7 | 7.3 |
| Victa | 9.0 | 9.0 |
| Merion | 8.7 | 9.0 |

*Disease severity based on a 9 point scale: 1 equals no disease; 9 equals 70–100 percent.

**Not statistically different at the 5 percent level.

TABLE TEN

Relative Comparisons for Resistance to Striped smut.

| CULTIVAR | STRIPED SMUT[1] |
|---|---|
| WTN-H6 | 0 |
| Adelphi | 0 |
| Baron | 2.3 |
| Geronimo | 53.3 |
| Park | 20.3 |
| Merion | 76.7 |

[1]Stripe Smut was rated as the estimated percent infected tillers within two 1-ft$^2$ squares per plot. The data is from 1977 at the University of Illinois, Urbana, Illinois.

Both the flag smut and stripe smut have occurred on the test plots in Palos Hills, Ill. Thus far, the smutted plants have been in plots surrounding the WTN-H6, but no infection of the smut organism has occurred in the plots containing the WTN-H6.

I claim:

1. The new and distinct variety of Bluegrass Plant herein described and illustrated and identified by the characteristics enumerated above.

* * * * *